United States Patent
Urbani (10) Patent No.: US 10,238,030 B2
(45) Date of Patent: Mar. 26, 2019

(54) WIRELESS MEDICAL DEVICE WITH A COMPLEMENTARY SPLIT RING RESONATOR ARRANGEMENT FOR SUPPRESSION OF ELECTROMAGNETIC INTERFERENCE

(71) Applicant: MEDTRONIC MINIMED, INC., Northridge, CA (US)

(72) Inventor: Fabio F. Urbani, Torrance, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 101 days.

(21) Appl. No.: 15/371,017

(22) Filed: Dec. 6, 2016

(65) Prior Publication Data
US 2018/0159234 A1    Jun. 7, 2018

(51) Int. Cl.
| H01Q 9/26 | (2006.01) |
| A01D 46/30 | (2006.01) |
| A01D 45/26 | (2006.01) |

(52) U.S. Cl.
CPC .......... *A01D 46/30* (2013.01); *A01D 45/263* (2013.01)

(58) Field of Classification Search
CPC .......... H01Q 1/38; H01Q 7/00; H01Q 17/008; H01Q 21/28; H01Q 9/265; H01Q 1/48; H01Q 21/30; H01Q 9/26; H01P 3/08; H01L 43/00
USPC ........................... 343/700 MS, 909, 893, 702
See application file for complete search history.

(56) References Cited

U.S. PATENT DOCUMENTS

| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |

(Continued)

FOREIGN PATENT DOCUMENTS

| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Hai V Tran
(74) *Attorney, Agent, or Firm* — Lorenz & Kopf, LLP (57) ABSTRACT

A medical device as described herein includes a communication module to process radio frequency signals associated with operation of the medical device, an antenna associated with the communication module, and a microstrip transmission component coupled between the communication module and the antenna. The transmission component includes a dielectric substrate, an electrically conductive signal trace formed overlying the upper major surface of the substrate, an electrically conductive ground plane formed overlying the lower major surface of the substrate, and a complementary split ring resonator arrangement integrally formed in the ground plane, and having a layout and dimensions tuned to cause the resonator arrangement to resonate at one or more harmonic frequencies of the nominal transmission frequency of the radio frequency signals.

20 Claims, 6 Drawing Sheets

(56) References Cited

U.S. PATENT DOCUMENTS

| | | |
|---|---|---|
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Feller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |

(56) References Cited

U.S. PATENT DOCUMENTS

| | | |
|---|---|---|
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,522,124 B2 * | 4/2009 | Smith .................... H01Q 15/02 343/873 |
| 8,208,973 B2 | 6/2012 | Mehta |
| 8,344,847 B2 | 1/2013 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2014/0266974 A1 * | 9/2014 | Sharawi ................. H01Q 21/28 343/893 |
| 2015/0070228 A1 * | 3/2015 | Gu ....................... H01Q 1/2283 343/727 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).

(56) References Cited

OTHER PUBLICATIONS

Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htrn.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117. pp. 1235-1241.
Gorton, L., et al., "Arnperometric Glucose Sensors Based on Immobilized Glucose-Oxidizing Enymes and Chemically Modified Electrodes," Analytica Chimica Acta. 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperornetric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al. "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7. Jul. 1983, pp. 526-532.
Monroe, D.,"Novel Implantable Glucose Sensors," ACL, Dec. 1989, pp. 8-16.
Morff, Robert J. et al., "Microfabrication of Reproducible, Economical, Electroenzyrnatic Glucose Sensors," Annuaal International Conference of teh IEEE Engineering in Medicine and Biology Society, Vo. 12, No. 2, 1990, pp. 483-434.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1933, pp. 165-172.
Nishida, Kenro, et al., "Clinical applications of teh wearable artificial endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.

(56) References Cited

OTHER PUBLICATIONS

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectornized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytics Chiniica Acta, vol. 218, 1989, pp. 137-142.

\* cited by examiner

WIRELESS MEDICAL DEVICE WITH A COMPLEMENTARY SPLIT RING RESONATOR ARRANGEMENT FOR SUPPRESSION OF ELECTROMAGNETIC INTERFERENCE

TECHNICAL FIELD

Embodiments of the subject matter described herein relate generally to wireless medical devices. More particularly, embodiments of the subject matter relate to techniques and components that reduce the emission of electromagnetic interference from wireless medical devices, as well as their susceptibility from unwanted electromagnetic radiation.

BACKGROUND

The prior art is replete with electronic devices that support wireless data communication. Wireless medical devices are useful for patients that have conditions that must be monitored on a continuous or frequent basis. For example, individuals with Type 1 diabetes and some individuals with Type 2 diabetes use insulin pumps to control their blood glucose levels. An insulin pump is one example of a medical fluid infusion device that can be designed to support wireless communication with other electronic devices, computer-based systems, or medical system components. For example, a wireless-enabled insulin pump can be configured to support any of the following functions: wirelessly receive control commands or instructions from another device; wirelessly transmit pump status data and/or patient data to another device; wirelessly receive glucose data from a continuous glucose sensor transmitter component; and wirelessly upload/download configuration data, updates, or settings from a server system.

Ideally, wireless medical devices should be designed to be relatively immune to electromagnetic interference and, conversely, should be designed to minimize the emission of unwanted electromagnetic radiation. In this regard, wireless devices must fulfill certain international standards and regulations related to the management of electromagnetic emissions, to ensure compatibility with neighboring electronic devices. Electromagnetic interference is a complex mechanism that takes place at different levels, including the chassis, circuit board, electronic component, and device level. Radiation sources typically include conductive trace coupling, cables attached to circuit boards, components such as chip packages and heat sinks, power busses, and other elements that can provide a low impedance current path.

Accordingly, it is desirable to have an efficient and effective approach to handle electromagnetic emission of a wireless-enabled electronic device, such as a wireless medical device. Furthermore, other desirable features and characteristics will become apparent from the subsequent detailed description and the appended claims, taken in conjunction with the accompanying drawings and the foregoing technical field and background.

BRIEF SUMMARY

An exemplary embodiment of a medical device is presented here. The medical device includes a radio frequency (RF) communication module to process RF signals associated with operation of the medical device, where the RF signals have a nominal transmission frequency. The medical device also includes an RF antenna associated with the RF communication module, and a microstrip transmission component coupled between the RF communication module and the RF antenna. The microstrip transmission component includes a dielectric substrate having an upper major surface and a lower major surface opposite the upper major surface, an electrically conductive signal trace formed overlying the upper major surface, an electrically conductive ground plane formed overlying the lower major surface, and a complementary split ring resonator (CSRR) arrangement integrally formed in the electrically conductive ground plane, and having a layout and dimensions tuned to cause the CSRR arrangement to resonate at the second harmonic frequency of the nominal transmission frequency.

Another exemplary embodiment of a medical fluid infusion device is also presented here. The medical device includes an RF communication module to process RF signals associated with operation of the medical device, where the RF signals have a nominal transmission frequency. The medical device also includes an RF antenna associated with the RF communication module, and a microstrip transmission component coupled between the RF communication module and the RF antenna. The microstrip transmission component includes a dielectric substrate having an upper major surface and a lower major surface opposite the upper major surface, an electrically conductive signal trace formed overlying the upper major surface, an electrically conductive ground plane formed overlying the lower major surface, and a CSRR arrangement for the microstrip transmission component. The CSRR arrangement has a layout and dimensions tuned to cause the CSRR arrangement to suppress the second harmonic frequency component of the nominal transmission frequency of the RF signals.

Another exemplary embodiment of a medical device is also presented here. The medical device includes an RF communication module to process RF signals associated with operation of the medical device, where the RF signals have a nominal transmission frequency. The medical device also includes an RF antenna associated with the RF communication module, and a microstrip transmission component coupled between the RF communication module and the RF antenna. The microstrip transmission component includes a dielectric substrate having an upper major surface and a lower major surface opposite the upper major surface, an electrically conductive signal trace formed on the upper major surface, and a layer of electrically conductive material formed on the lower major surface. The layer of electrically conductive material includes voids formed therein to define a CSRR arrangement having a layout and dimensions tuned to cause the CSRR arrangement to resonate at the second harmonic frequency of the nominal transmission frequency.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures. The drawings are not to scale, and the dimensions of certain features have been exaggerated for clarity and ease of description.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard," and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

The subject matter described here generally relates to the management of electromagnetic interference associated with the operation of wireless electronic devices, such as wireless medical devices. The solution presented here can be applied to any medical device using wireless communication that requires immunity and low emission of electromagnetic radiation (e.g., a defibrillator device, a pacemaker device, or the like). Although the subject matter described here can be implemented in a variety of different wireless devices, the exemplary embodiment presented here is a wireless medical fluid infusion device of the type used to treat a medical condition of a patient. The medical fluid infusion device is used for infusing a medication fluid into the body of a user. The non-limiting example described below relates to a medical device used to treat diabetes (more specifically, an insulin infusion pump), although embodiments of the disclosed subject matter are not so limited. Accordingly, the medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like.

For the sake of brevity, conventional features and functionality related to infusion systems, insulin pumps, and their wireless communication capabilities may not be described in detail here. Examples of fluid infusion pumps having wireless features may be of the type described in, but not limited to, U.S. Pat. Nos. 8,208,973 and 8,344,847, which are herein incorporated by reference.

Figure 1:
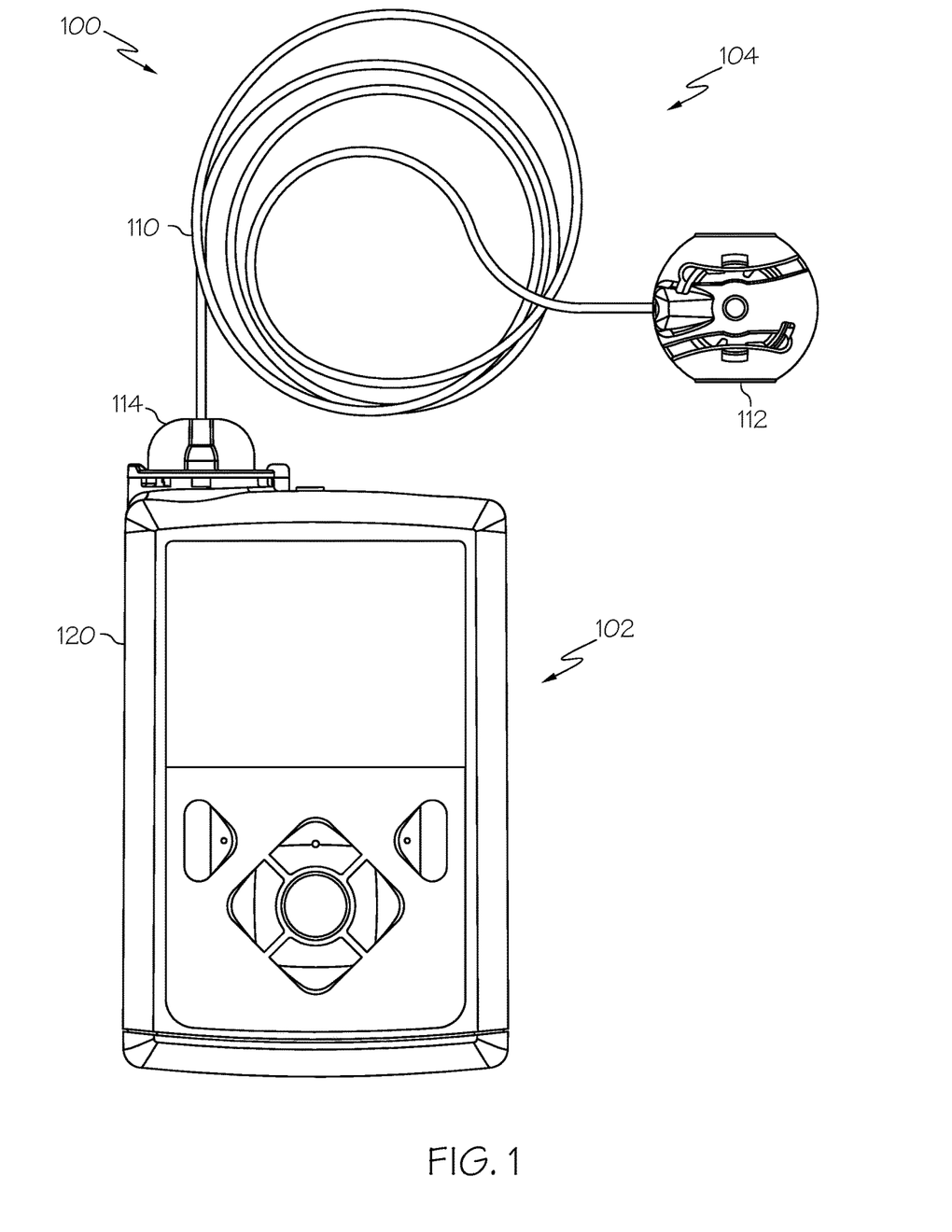
FIG. 1 is a plan view of an exemplary embodiment of a fluid delivery system that includes a medical fluid infusion device and an infusion set.

Referring to the drawings, FIG. 1 is a plan view of an exemplary embodiment of a fluid delivery system 100 that includes a portable medical fluid infusion device 102 and a fluid conduit assembly that takes the form of an infusion set 104. For this particular embodiment, the infusion set 104 can be coupled to the fluid infusion device 102 as depicted in FIG. 1. The fluid infusion device 102 accommodates a fluid reservoir (hidden from view in FIG. 1) for the medication fluid to be delivered to the user.

The illustrated embodiment of the infusion set 104 includes, without limitation: a length of tubing 110; an infusion unit 112 coupled to the distal end of the tubing 110; and a connector 114 coupled to the proximal end of the tubing 110. The fluid infusion device 102 is designed to be carried or worn by the patient, and the infusion set 104 terminates at the infusion unit 112 such that the fluid infusion device 102 can deliver fluid to the body of the patient via the tubing 110. The infusion unit 112 includes a cannula (hidden from view in FIG. 1) that is coupled to the distal end of the tubing 110. The cannula is inserted into the skin and is held in place during use of the fluid infusion device 102.

The infusion set 104 defines a fluid flow path that fluidly couples the fluid reservoir to the infusion unit 112. The connector 114 mates with and couples to a section of the fluid reservoir, which in turn is coupled to a housing 120 of the fluid infusion device 102. The connector 114 establishes the fluid path from the fluid reservoir to the tubing 110. Actuation of the fluid infusion device 102 causes the medication fluid to be expelled from the fluid reservoir, through the infusion set 104, and into the body of the patient via the infusion unit 112 and cannula at the distal end of the tubing 110. Accordingly, when the connector 114 is installed as depicted in FIG. 1, the tubing 110 extends from the fluid infusion device 102 to the infusion unit 112, which in turn provides a fluid pathway to the body of the patient.

The fluid infusion device 102 includes a radio frequency (RF) antenna to support wireless data communication with other devices, systems, and/or components. The RF antenna can be located inside the housing 120 or it can be integrally formed with the housing 120. Accordingly, the RF antenna is hidden from view in FIG. 1.

Figure 2:
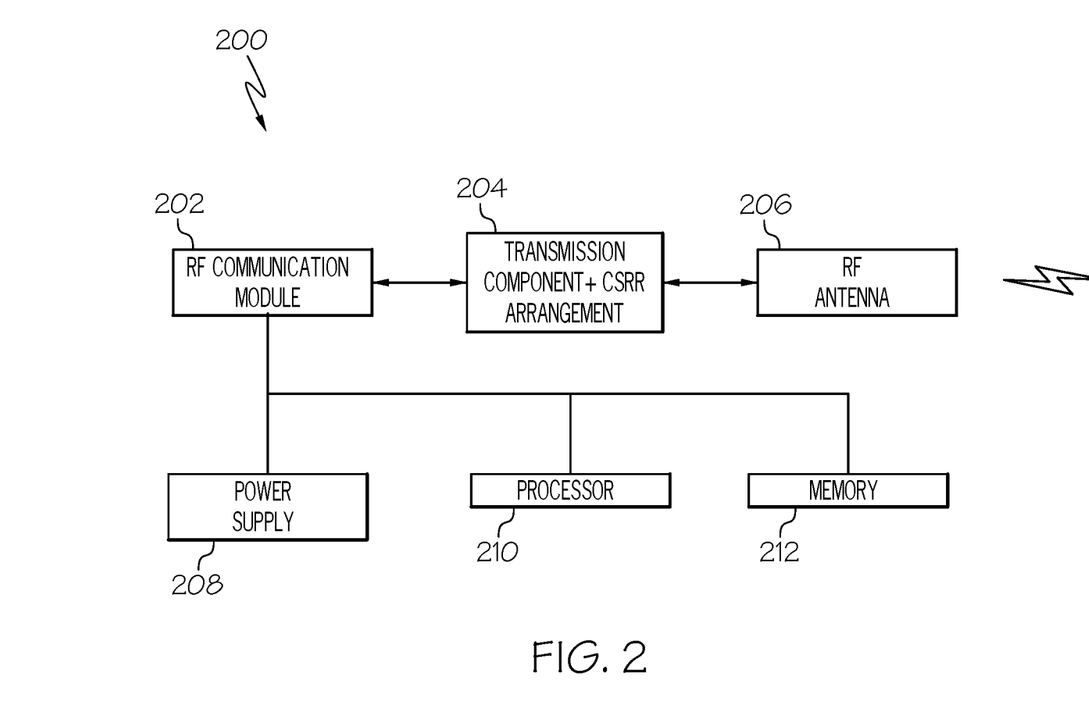
FIG. 2 is a schematic block diagram representation of a wireless communication subsystem suitable for use with the medical fluid infusion device shown in FIG. 1.

FIG. 2 is a schematic block diagram representation of a wireless communication subsystem 200 suitable for use with the medical fluid infusion device 102 shown in FIG. 1. It should be apparent that FIG. 2 depicts the wireless communication subsystem 200 in a very simplified manner, and that a practical embodiment of the fluid infusion device 102 will of course include many additional features and components. The wireless communication subsystem 200 generally includes, without limitation: an RF communication module 202; a transmission component 204; an RF antenna 206 coupled to the RF communication module 202 by way of the transmission component 204; a power supply 208; a processor 210; and an appropriate amount of memory 212. As explained in more detail below, an exemplary embodiment of the transmission component 204 includes a complementary split ring resonator (CSRR) arrangement incorporated therein. The various operating elements of the wireless communication subsystem 200 are coupled together as needed to facilitate the delivery of operating power from the power supply 208, the transfer of data, the transfer of control signals and commands, and the like.

The RF communication module 202 is suitably configured to process RF signals associated with the operation of the fluid infusion device 102, and to otherwise support the wireless communication functions of the fluid infusion device 102. In this regard, the RF communication module 202 may include a transceiver or radio element that generates RF signals suitable for transmission, and that is capable of receiving RF signals generated by neighboring devices, systems, or components. Thus, the RF communication module 202 is suitably configured to generate the RF signals to be transmitted by the antenna 206. For the exemplary embodiment described herein, the RF communication module 202 is designed to operate in the ultra-high frequency (UHF) band. Alternate embodiments may instead utilize other RF bands or frequencies as appropriate. In certain practical embodiments, the RF communication module 202 and the RF antenna are designed and tuned to accommodate RF signals having a nominal transmission frequency centered around 2.4 GHz. In this regard, the RF communication module 202 and the RF antenna 206 can be suitably configured to handle RF signals having frequencies within the range of about 2.402 GHz to about 2.480 GHz.

The RF antenna 206 is operationally associated with the RF communication module 202. Thus, the RF antenna 206 can be designed, configured, and tuned to accommodate the particular operating frequency band utilized by the RF communication module 202. The RF antenna 206 is suitably configured to transmit and receive RF energy associated with the operation of the host electronic device. Accordingly, the transmission component 204 is coupled between the RF communication module 202 and the RF antenna 206 to convey RF signals in a bidirectional manner. As described in more detail below, the transmission component 204 can be realized as a microstrip transmission line having an electrically conductive signal trace fabricated on the upper surface of a dielectric substrate, and having an electrically conductive ground plane fabricated on the lower surface of the dielectric substrate. Moreover, the wireless communication subsystem 200 includes a CSRR arrangement that is preferably realized as an integrated feature of the transmission component 204.

The power supply 208 may be a disposable or rechargeable battery, a set of batteries, or a battery pack that is rated to provide the necessary voltage and energy to support the operation of the wireless communication subsystem 200. Alternatively or additionally, the power supply 208 may receive power from an external source such as an ordinary AC outlet, a portable charger, or the like. In a typical implementation, the power supply 208 also provides operating energy to other components and subsystems of the host device.

The processor 210 may be any general purpose microprocessor, controller, or microcontroller that is suitably configured to control the operation of the host device, including the wireless communication subsystem 200. In practice, the processor 210 may execute one or more software applications or instruction sets that provide the desired functionality for the host device. In this regard, the processor 210 can control, manage, and regulate the generation and transmission of outgoing RF signals, and the receipt and handling of incoming RF signals as needed.

The memory 212 may be realized as any processor-readable medium, including an electronic circuit, a semiconductor memory device, a ROM, a flash memory, an erasable ROM, a floppy diskette, a CD-ROM, an optical disk, a hard disk, an organic memory element, or the like. For example, the memory 212 is capable of storing application software utilized by the host device and/or data utilized by the host device during operation, e.g., physiological data of the patient, device status data, control commands, configuration setting data, and the like.

In certain embodiments, the medical fluid infusion device 102 and the wireless communication subsystem 200 utilize circuit boards to mount electronic components and to implement conductive traces, signal paths, and voltage supply lines. In this regard, operating power/energy can be provided by power planes embedded in a multilayer structure of a circuit board. Such power planes can induce electromagnetic radiation in a manner that is highly analogous to the way microstrip antennas radiate RF energy. In a microstrip patch antenna and in a printed circuit board, radiation is induced by a time-varying fringing electric field at the edges of the board. It is desirable to have a low cost electromagnetic filtering technique that also reduces the size and footprint of traditional electromagnetic interference filter components.

The concept presented here utilizes the conductive ground plane of the transmission component 204 to form periodic or quasi-periodic structures with electromagnetically controllable properties and characteristics. More specifically, the transmission component 204 is suitably designed and fabricated to include sub-wavelength resonators that are configured to reduce electromagnetic interference. In this regard, the conductive ground plane is carefully fabricated to create a CSRR arrangement, which can be deployed as an alternative to microstrip stopband structures. The CSRR arrangement preferably includes a plurality of identical CSRR elements that cooperate to suppress certain RF signal frequencies, in particular, the second harmonic frequency of the RF signals of interest (which are transmitted and received by the host electronic device). For the exemplary embodiment described here, the CSRR arrangement is shaped, sized, dimensioned, and otherwise configured in accordance with the targeted pass band frequency range of 2.402 to 2.480 GHz, and in accordance with the targeted stop band frequency range of 4.804 to 4.960 GHz. It should be understood that the particular pass band and stop band frequency ranges will be dictated by the specific wireless protocol utilized by the host device. In this regard, a number of standard RF integrated circuit radios for medical device deployment use the 2.4 GHz industrial, scientific, and medical (ISM) band which implies the 4.804 to 4.960 GHz bandwidth. In practice, additional stop bands can be implemented by including multiple CSRRs of different sizes.

Figure 3:
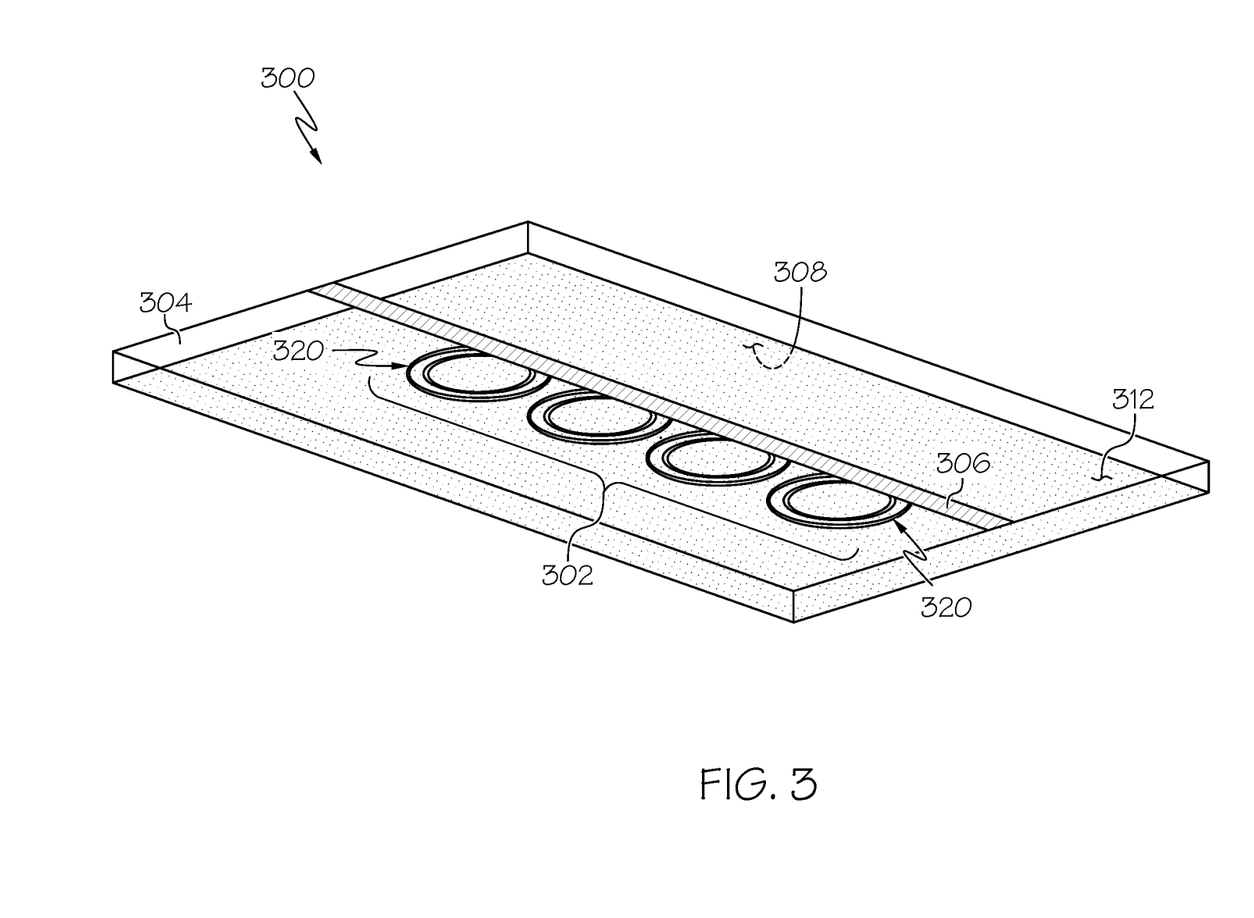
FIG. 3 is a perspective phantom view of a microstrip transmission component having a complementary split ring resonator (CSRR) arrangement integrally formed therein.
Figure 4:
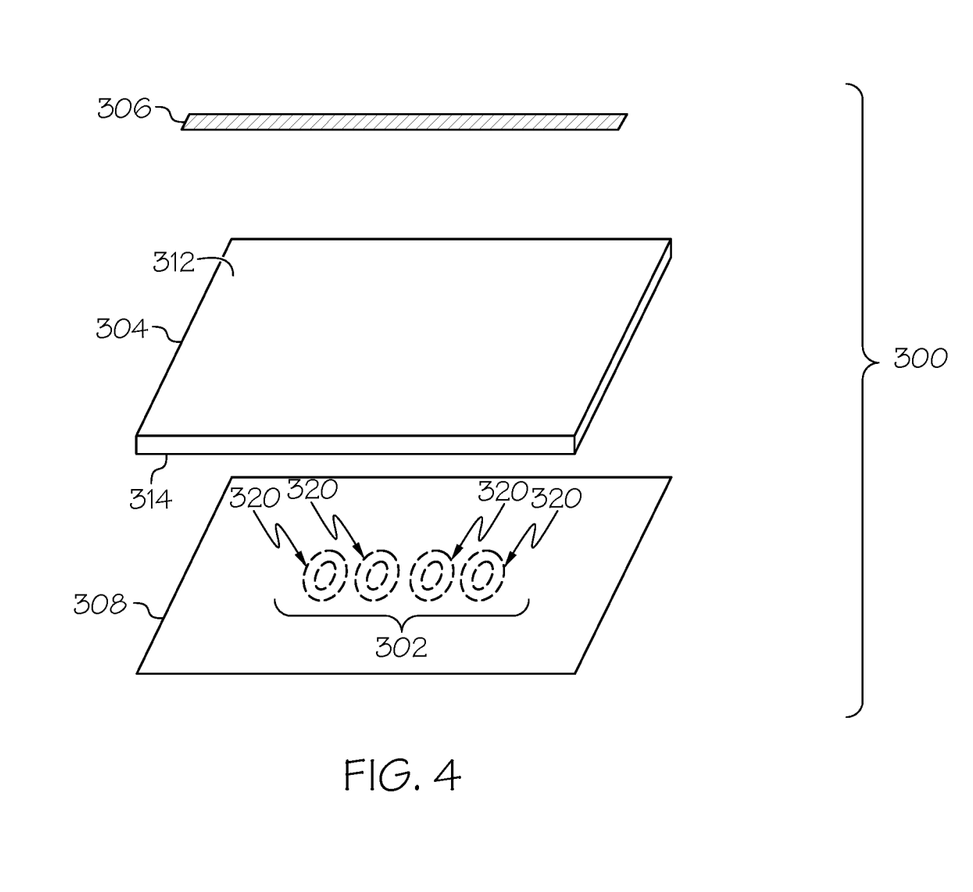
FIG. 4 is an exploded perspective view of the microstrip transmission component shown in FIG. 3.
Figure 5:
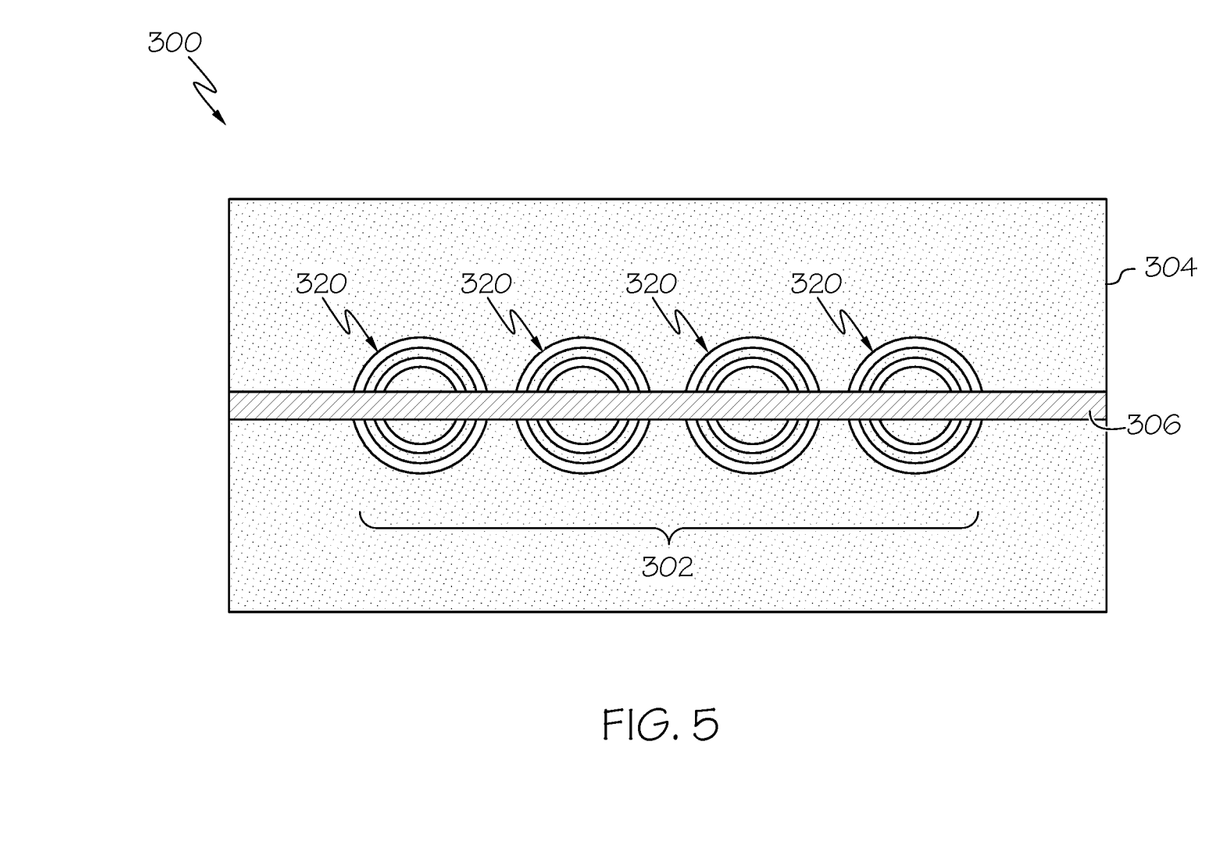
FIG. 5 is a top phantom view of the microstrip transmission component shown in FIG. 3.

FIG. 3 is a perspective phantom view of a microstrip transmission component 300 having a CSRR arrangement 302 integrally formed therein, FIG. 4 is an exploded perspective view of the microstrip transmission component 300, and FIG. 5 is a top phantom view of the microstrip transmission component 300. The microstrip transmission component 300 is depicted in a simplified manner for clarity and ease of description. The shape, size, and topology of the microstrip transmission component 300 can vary as needed for the particular embodiment.

The microstrip transmission component 300 generally includes, without limitation: a dielectric substrate 304; an electrically conductive signal trace 306; and an electrically conductive ground plane 308. For this particular embodiment, the CSRR arrangement 302 is integrally formed in the ground plane 308. The dielectric substrate 304 is formed from a suitable dielectric or insulating material such as, without limitation, plastic, an FR-4 circuit board material, a ceramic material, a flexible vinyl material, or the like. In some embodiments, the dielectric substrate 304 is a distinct component of the wireless communication subsystem 200, as schematically depicted in FIG. 2. In other embodiments, the dielectric substrate 304 can be realized as an integrated part of the housing 120, an internal structure, or other part of the fluid infusion device 102.

The dielectric constant of the substrate 304 can be chosen to obtain the desired electromagnetic characteristics. For example, the substrate 304 can be formed from a material having a dielectric constant within the range of about 3.0 to 12.0. In accordance with certain exemplary embodiments, the substrate 304 is formed from a thin FR-4 material having a specified dielectric constant of 4.4. The thickness (i.e., the height dimension relative to the perspective shown in FIG. 3) of the substrate 304 can also vary from one embodiment to another, as appropriate to achieve the desired electromagnetic characteristics. The embodiment mentioned here employs an FR-4 substrate 304 having a nominal thickness of 1.0 mm.

The dielectric substrate 304 has an upper major surface 312 and a lower major surface 314 opposite the upper major surface 312 (see FIG. 4, which depicts the signal trace 306 and the ground plane 308 separated from the dielectric substrate 304). The electrically conductive signal trace 306 is formed overlying the upper major surface 312, and the electrically conductive ground plane 308 is formed overlying the lower major surface 314. For the illustrated embodiment, the signal trace 306 is formed directly on the upper major surface 312, and the ground plane 308 is formed directly on the lower major surface 314. The signal trace 306 and the ground plane 308 can be formed from an electrically conductive material such as, without limitation, copper, aluminum, gold, alloys thereof, or the like. In practice, the signal trace 306 and the ground plane 308 are formed from respective layers of electrically conductive material that reside on the dielectric substrate 304. The signal trace 306 can be fabricated by the selective removal of portions of the electrically conductive material on the upper major surface 312, e.g., by a conventional etching procedure. Likewise, the CSRR arrangement 302 can be defined by voids formed in the electrically conductive material on the lower major surface 314. Thus, the spaces corresponding to the CSRR arrangement 302 can be fabricated by the selective removal of portions of the electrically conductive material on the lower major surface 314, e.g., by a conventional etching procedure. Etching away the conductive material on the lower major surface 314 represents one suitable process for integrally forming the CSRR arrangement 302 in the electrically conductive ground plane 308.

The CSRR arrangement 302 has a layout and dimensions that are tuned to cause the CSRR arrangement 302 to resonate at the second harmonic frequency of the nominal transmission frequency of the RF signals carried by the microstrip transmission component 300. As mentioned above, the exemplary embodiment described here considers a nominal transmission frequency of 2.40 GHz, having a second harmonic frequency of 4.80 GHz. Thus, the layout and dimensions of the CSRR arrangement are tuned to cause the CSRR arrangement to suppress or filter frequencies in a band centered around 4.80 GHz.

Although not always required, the illustrated embodiment of the CSRR arrangement 302 includes a plurality of CSRR elements 320 in series with one another. The depicted embodiment includes four CSRR elements 320, which are all identical in layout and in their dimensions. As best shown in FIG. 5 (which is a top phantom view of the microstrip transmission component 300), the CSRR elements 320 are arranged such that they are all centered in alignment with the electrically conductive signal trace 306. In other words, the top-down (or, equivalently, the bottom-up) projection of the signal trace 306 has a longitudinal axis that intersects the centers of the CSRR elements 320. This arrangement is desirable to optimize the RF coupling between the signal trace and the CSRR elements 320.

A split ring resonator (SRR) is a resonant element having a high quality factor at microwave frequencies. An SRR is fabricated from concentric electrically conductive split rings. When an SRR is excited by an external time varying magnetic field applied parallel to the ring axis, an electromotive force around the SRR is generated, which gives rise to current loops in the SRR. These current loops are closed through the distributed capacitance between the concentric rings. In this regard, an SRR behaves as an externally driven LC circuit with a resonant frequency that can be tuned by varying certain dimensions of the SRR.

By invoking the concepts of duality and complementarity, a CSRR can be derived from an SRR structure in a straightforward way. In planar technology, a CSRR can be defined as the negative of an SRR. Accordingly, a CSRR exhibits an electromagnetic behavior that is almost the dual of that of an SRR. More specifically, a negative-$\varepsilon$ effective permittivity can be expected for any CSRR-based medium, whereas a negative-$\mu$ behavior arises in an equivalent SRR system. In other words, an SRR can be considered to be a resonant magnetic dipole that can be excited by an axial magnetic field, while a CSRR essentially behaves as an electric dipole (with the same frequency of resonance) that can be excited by an axial electric field. The latter characteristic makes a CSRR an ideal candidate for microstrip technology implementation.

Figure 6:
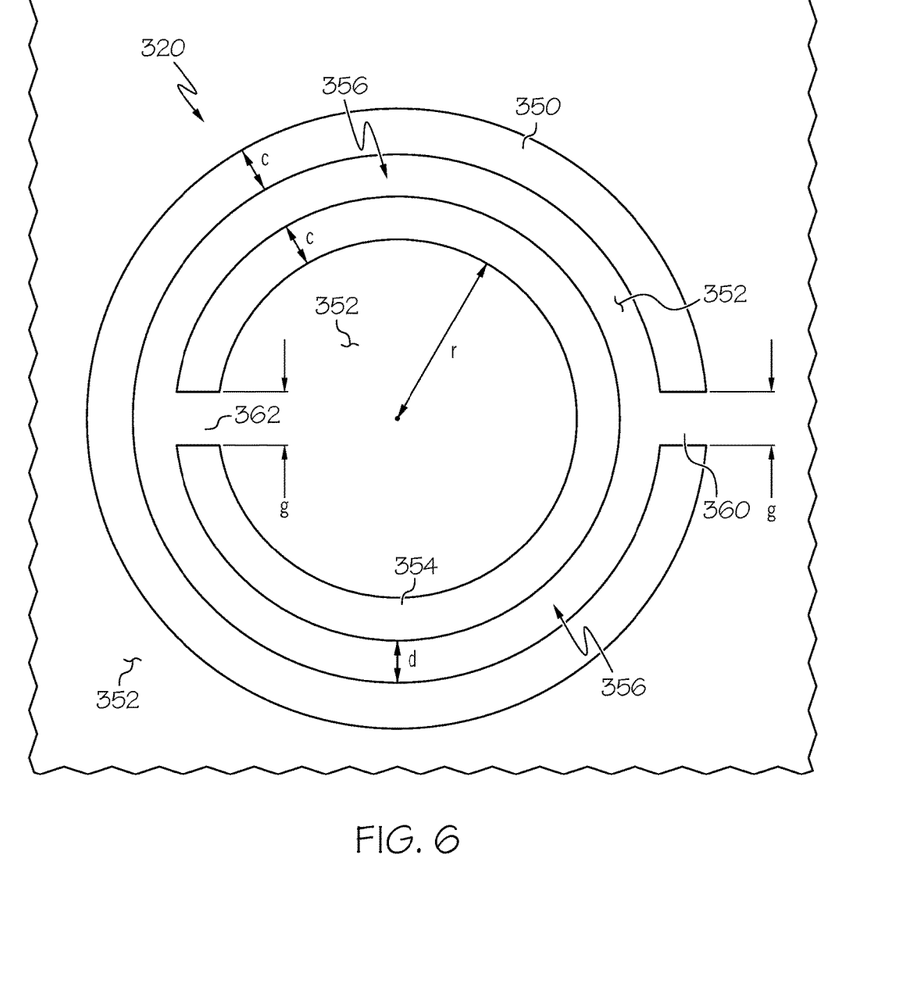
FIG. 6 is a plan view of an exemplary embodiment of a CSRR element suitable for use with the microstrip transmission component shown in FIG. 3.

Materials with negative permeability and/or negative permittivity are known as metamaterials (MTMs). The concept of MTMs plays an important role in science and technology due to the large applicability of MTMs in the development of efficient devices. MTMs are artificial structures with electromagnetic properties different from conventional materials. They are constructed to accomplish specifically desired physical properties such as negative permeability and/or negative permittivity, and/or to alter the electromagnetic response of a device for the frequency region of interest. Most metamaterials include scattering element arrays embedded in a host matrix. The scattering elements are typically identical, and the electromagnetic properties of the medium can be inferred from the properties of the unit cell (formed by one repeated element as depicted in FIG. 6). This characteristic allows the designer to engineer the effective electromagnetic parameters of the medium by modifying the size, shape, and composition of the unit cell.

CSRRs are sub-lambda structures, i.e., their dimensions are electrically small at the resonant frequency (typically $\leq \lambda_g/10$). As used here, $\lambda_g$ is the guide wavelength in the guiding structure (e.g., microstrip) as opposed to the wavelength in free space. Due to the small electrical dimensions, a high level of miniaturization is expected when using CSRRs. Moreover, the proposed stopband arrangement described herein has the advantage of an easier and low-cost implementation in microstrip technology, because coupling between the CSRR arrangement 302 and the electrically conductive signal trace 306 can be simply achieved by etching the CSRR elements 320 directly in the conductive ground plane 308.

The CSRR elements 320 (and, therefore, the CSRR arrangement 302) and/or the microstrip transmission component 300 can be tuned to resonate at the desired frequency or frequency band. More specifically, any of the following parameters can be adjusted individually or in any desired combination: the type of dielectric material (and, inherently, the dielectric constant) used for the dielectric substrate 304; the thickness/height of the dielectric substrate 304; the type of conductive material used for the signal trace 306; the type of conductive material used for the ground plane 308; the overall shape of each CSRR element 320; the number of CSRR elements 320 deployed; the location of the CSRR elements 320 relative to the signal trace 306; the array period used for the CSRR elements 320 (i.e., the distance between neighboring CSRR elements 320); the width of the signal trace 306; and certain dimensions of the CSRR elements 320. In this regard, FIG. 6 is a plan view of an exemplary embodiment of a CSRR element 320; FIG. 6 employs an exaggerated scale for ease of illustration.

As mentioned above, each CSRR element 320 in the CSRR arrangement 302 is identically configured as depicted in FIG. 6. The CSRR element 320 includes an outer split ring shaped void 350 formed in the electrically conductive material 352, and an inner split ring shaped void 354 formed in the electrically conductive material 352. The inner split ring shaped void 354 resides in an interior space 356 defined by the outer split ring shaped void 350, and the two split ring shaped voids 350, 354 are concentric. The outer split ring shaped void 350 defines a gap 360, wherein the electrically conductive material 352 fills the gap 360. Similarly, the inner split ring shaped void 354 defines a gap 362, wherein the electrically conductive material 352 fills the gap 362.

FIG. 6 includes labels that indicate certain tunable dimensions of the CSRR element 320. The labels and their corresponding dimensions are listed below:

r=innermost radius of the inner split ring shaped void 354;
c=line width of the inner split ring shaped void 354, which equals the line width of the outer split ring shaped void 350 for this particular embodiment;
d=line width (separation distance) between the inner split ring shaped void 354 and the outer split ring shaped void 350;
g=distance of the gap 360 of the outer split ring shaped void, which equals the distance of the gap 362 of the inner split ring shaped void for this particular embodiment.

Any of the above dimensions can be adjusted to tune the electromagnetic performance of the CSRR arrangement 302. Moreover, the dielectric constant of the substrate 304, the height of the substrate 304, the line width of the signal trace 306, and the center-to-center distance between neighboring CSRR elements 320 (i.e., the array period) can be adjusted to tune the electromagnetic characteristics and properties of the CSRR arrangement 302. In particular, any one or any combination of these parameters can be adjusted to influence the passband of the microstrip transmission component 300, the stopband (resonant frequency band) of the CSRR arrangement 302, and the like.

In accordance with certain exemplary embodiments, the dielectric substrate 304 is formed from a thin FR-4 board having a thickness of 1.0 mm, and having a dielectric constant of 4.4. For this particular embodiment: the line width of the signal trace 306 is 1.9 mm; the line widths for c, d, and g are all equal to 0.25 mm; the radius r equals 1.75 mm; and the array period equals 5.83 mm. Simulated results for a microstrip transmission component 300 having this configuration indicate a stopband (−20.0 dB rejection) of 4.60 GHz to 5.29 GHz, which encompasses the first harmonic frequency of the desired RF signals (4.80 GHz). Therefore, a wireless electronic device, such as a medical fluid infusion device, can utilize the microstrip transmission component 300 to facilitate the communication of RF signals at the nominal transmission frequency of 2.4 GHz while effectively suppressing unwanted frequency components centered around the first harmonic frequency of 4.8 GHz. Of course, the dimensions outlined above are merely exemplary, and an embodiment of the microstrip transmission component 300 can utilize a CSRR arrangement 302 having alternative specifications if so desired, especially if needed to reject or suppress a different frequency band.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A medical device comprising:
   a housing;
   a radio frequency (RF) communication module to process RF signals associated with operation of the medical device, the RF signals having a nominal transmission frequency;
   an RF antenna associated with the RF communication module, the RF antenna integrally formed with the housing;
   a physically distinct microstrip transmission component coupled between the RF communication module and the RF antenna, the microstrip transmission component comprising:
   a dielectric substrate having an upper major surface and a lower major surface opposite the upper major surface;
   an electrically conductive signal trace formed overlying the upper major surface;
   an electrically conductive ground plane formed overlying the lower major surface; and
   a complementary split ring resonator (CSRR) arrangement integrally formed in the electrically conductive ground plane, and having a layout and dimensions tuned to cause the CSRR arrangement to resonate at a harmonic frequency of the nominal transmission frequency.

2. The medical device of claim 1, wherein the CSRR arrangement comprises a plurality of CSRR elements in series and centered in alignment with the electrically conductive signal trace.

3. The medical device of claim 2, wherein the CSRR elements are identical in layout and dimensions.

4. The medical device of claim 1, wherein:
   the RF communication module and the RF antenna accommodate RF signals having the nominal transmission frequency centered around 2.4 GHz; and the layout and dimensions of the CSRR arrangement are tuned to cause the CSRR arrangement to resonate at a frequency centered around 4.8 GHz.

5. The medical device of claim 1, wherein:
the electrically conductive signal trace is formed directly on the upper major surface; and
the electrically conductive ground plane is formed directly on the lower major surface.

6. The medical device of claim 1, wherein:
the electrically conductive ground plane comprises a layer of electrically conductive material formed directly on the lower major surface; and
the CSRR arrangement is defined by voids formed in the electrically conductive material.

7. The medical device of claim 1, wherein:
the electrically conductive ground plane comprises a layer of electrically conductive material formed directly on the lower major surface; and
the CSRR arrangement is defined by selective removal of portions of the electrically conductive material.

8. A medical fluid infusion device comprising:
a housing;
a radio frequency (RF) communication module to process RF signals associated with operation of the medical device, the RF signals having a nominal transmission frequency;
an RF antenna associated with the RF communication module, the RF antenna integrally formed with the housing;
a physically distinct microstrip transmission component coupled between the RF communication module and the RF antenna, the microstrip transmission component comprising:
a dielectric substrate having an upper major surface and a lower major surface opposite the upper major surface;
an electrically conductive signal trace formed overlying the upper major surface; and
an electrically conductive ground plane formed overlying the lower major surface; and
a complementary split ring resonator (CSRR) arrangement for the microstrip transmission component, the CSRR arrangement having a layout and dimensions tuned to cause the CSRR arrangement to suppress a harmonic frequency component of the nominal transmission frequency of the RF signals.

9. The medical fluid infusion device of claim 8, wherein the CSRR arrangement comprises a plurality of CSRR elements in series and centered in alignment with the electrically conductive signal trace.

10. The medical fluid infusion device of claim 8, wherein:
the electrically conductive signal trace is formed directly on the upper major surface; and
the electrically conductive ground plane is formed directly on the lower major surface.

11. The medical fluid infusion device of claim 8, wherein the layout and dimensions of the CSRR arrangement are tuned to cause the CSRR arrangement to resonate at the harmonic frequency.

12. The medical fluid infusion device of claim 8, wherein the CSRR arrangement is integrally formed in the electrically conductive ground plane.

13. The medical fluid infusion device of claim 12, wherein:

the electrically conductive ground plane comprises a layer of electrically conductive material formed directly on the lower major surface; and
the CSRR arrangement is defined by voids formed in the electrically conductive material.

14. The medical fluid infusion device of claim 12, wherein:
the electrically conductive ground plane comprises a layer of electrically conductive material formed directly on the lower major surface; and
the CSRR arrangement is defined by selective removal of portions of the electrically conductive material.

15. A medical device comprising:
a housing;
a radio frequency (RF) communication module to process RF signals associated with operation of the medical device, the RF signals having a nominal transmission frequency;
an RF antenna associated with the RF communication module, the RF antenna integrally formed with the housing;
a physically distinct microstrip transmission component coupled between the RF communication module and the RF antenna, the microstrip transmission component comprising:
a dielectric substrate having an upper major surface and a lower major surface opposite the upper major surface;
an electrically conductive signal trace formed on the upper major surface; and
a layer of electrically conductive material formed on the lower major surface, the layer of electrically conductive material comprising voids formed therein to define a complementary split ring resonator (CSRR) arrangement having a layout and dimensions tuned to cause the CSRR arrangement to resonate at a harmonic frequency of the nominal transmission frequency.

16. The medical device of claim 15, wherein the layer of electrically conductive material serves as a ground plane for the electrically conductive signal trace.

17. The medical device of claim 15, wherein the CSRR arrangement comprises a plurality of CSRR elements in series and centered in alignment with the electrically conductive signal trace.

18. The medical device of claim 17, wherein the CSRR elements are identical in layout and dimensions.

19. The medical device of claim 17, wherein each of the CSRR elements comprises:
an outer split ring shaped void formed in the electrically conductive material; and
an inner split ring shaped void formed in the electrically conductive material, the inner split ring shaped void residing in an interior space defined by the outer split ring shaped void, and the inner split ring shaped void being concentric with the outer split ring shaped void.

20. The medical device of claim 17, wherein:
the outer split ring shaped void has a first line width;
the inner split ring shaped void has a second line width;
the outer split ring shaped void is separated from the inner split ring shaped void by a third line width; and
the first line width, the second line width, and the third line width are equal.

* * * * *